United States Patent
Bernard et al.

(10) Patent No.: US 6,929,685 B2
(45) Date of Patent: Aug. 16, 2005

(54) ALKYLAMINE DERIVATIVES AS ANTIFOULING AGENTS

(75) Inventors: Daniel Bernard, Courbevoie (FR); Jean-Claude Braekman, Rode-Sainte-Genèse (BE); Gabriele Ferrari, AB Den Helder (NL); Martin Kugler, Leichlingen (DE); Franz Kunisch, Odenthal (DE); Mark Plehiers, Brussels (BE); Marcel Vos, HS Huizen (NL)

(73) Assignee: Bayer Atiengesellschaft (DE)

( * ) Notice: Subject to any disclaimer, the term of this patent is extended or adjusted under 35 U.S.C. 154(b) by 0 days.

(21) Appl. No.: 10/473,172

(22) PCT Filed: Mar. 27, 2002

(86) PCT No.: PCT/EP02/03763

§ 371 (c)(1),
(2), (4) Date: Jan. 14, 2004

(87) PCT Pub. No.: WO02/076928

PCT Pub. Date: Oct. 3, 2002

(65) Prior Publication Data

US 2004/0118318 A1 Jun. 24, 2004

(30) Foreign Application Priority Data

Mar. 27, 2001 (EP) .............................................. 01107581

(51) Int. Cl.$^7$ ........................ A01N 33/02; A01N 37/30; A01N 47/40; C09D 5/16
(52) U.S. Cl. ................. 106/18.32; 106/18.33; 424/405; 514/638; 514/663; 514/665; 514/667; 514/672; 514/740; 523/177
(58) Field of Search ............................ 106/18.32, 18.33; 424/405; 514/638, 663, 665, 667, 672, 740; 523/177

(56) References Cited

U.S. PATENT DOCUMENTS

| 3,285,809 A | 11/1966 | Mod et al. |
| 4,439,555 A | 3/1984 | Doi et al. |
| 5,503,836 A | 4/1996 | Fellers et al. |
| 5,814,668 A | 9/1998 | Whittemore et al. |
| 6,030,971 A | 2/2000 | Whittemore et al. |

FOREIGN PATENT DOCUMENTS

| JP | 53104729 | 9/1978 |
| JP | 2002-370907 A | * 12/2002 |
| WO | WO 97/09464 A2 | 3/1997 |

OTHER PUBLICATIONS

Kazuo Ina et al., "Isothiocyanates As An Attaching Repellent Against The Blue Mussel Mytilus Edulis," Agricultural And Biological Chemistry., vol. 53, No. 12, Pg. 3323–3325, Dec. 1989.

* cited by examiner

Primary Examiner—Anthony J. Green
(74) Attorney, Agent, or Firm—Edell, Shapiro & Finnan, LLP

(57) ABSTRACT

The invention relates to methods for preventing the attachment of aquatic organisms to surfaces that are submerged for extension periods of time in water. More particularly, this invention relates to the protection of submerged surfaces with alkylamine derivatives as antifouling agents. The invention is beneficiary for the environment in that it will permit the use of copper- and tin-free paints.

16 Claims, No Drawings

ALKYLAMINE DERIVATIVES AS ANTIFOULING AGENTS

FIELD OF INVENTION

The invention relates to methods for preventing the attachment of aquatic organisms to surfaces that are submerged for extensive periods of time in water. More particularly, this invention relates to the protection of submerged surfaces and underwater constructions with alkylamines derivatives as antifouling agents.

BACKGROUND OF THE INVENTION

The ever recurring growth of fouling organisms on underwater structures such as ships, docks, piers, pilings, fishnets, heat exchangers, dams, piping structures, intake screens, cooling towers and the like is a costly and hazardous problem in both marine and freshwater applications. The presence of fouling organisms such as barnacles, zebra mussels, algae, diatoms, hydroids, bryozoa, ascidians, tubeworms, Asiatic clams and the like causes economic damage in various ways: for example, attachment to the hulls of ships reduces fuel efficiency and causes loss of profitable sailing time because of the need to clean the hulls. Similarly, the attachment of these organisms to cooling water equipment decreases heat conductivity, which eventually reduces or blocks the cooling power of the equipment and drives up costs.

A variety of agents useful for controlling fouling organisms in fresh water or seawater have been used to prevent the attachment and overgrowth of these organisms.

A common method of controlling the presence or attachment of fouling organisms is to coat or permeate the underwater structure with a composition that comprises mixtures of toxic compounds such as tri-n-butyl tin or copper compounds. Antifouling agents in the form of paint can contain up to 60% by weight of the active ingredients and can be used to paint surfaces such as the underwater hull of ships. The paint prevents attachment and growth of fouling organisms by continuously releasing antifouling agents underwater. The disadvantage of many of the present antifouling agents is that they are persistent in the environment, are often acutely toxic and degrade too slowly in aquatic environments and are, therefore, ecologically harmful. Hazardous antifouling agents can eventually bioaccumulate and enter the food chain and therefore represent a threat to marine and human life.

For example, it is well established that heavy metal compounds, especially organotin compounds that are widely used as antifouling agents, accumulate in mussels.

It is an object of this invention to provide an environmentally and ecologically sound method of combating or controlling marine and freshwater fouling organisms.

It is another object of this invention to provide an effective method for protecting aquatic structures against fouling by marine or freshwater fouling organisms.

It is a further object of this invention to provide antifoulant compositions that comprises certain alkylamine derivatives as the active agents. The advantage of these agents is that they are tin and copper free and less toxic to non-target organisms than the existing antifouling compounds. They are also biodegradable so that they are less bioaccumulated and therefore ecologically safer.

SUMMARY OF THE INVENTION

The present invention provides a method to prevent settlement on surfaces by marine or freshwater fouling organisms which comprises contacting said organisms or the locus thereof with an effective amount of one or more antifouling compounds of which at least one compound of formula (I) or (II)

$$XCH_2—CHX—(CH_2)_n—CH_2R^1 \quad (I)$$

$$CH_2=CH—(CH_2)_n—CH_2R^1 \quad (II)$$

wherein
$R^1$ represents an isonitrile or isocyanate moiety, or $NR^2R^3$ wherein
$R^2$ represents a hydrogen atom or C1–C8 alkyl and
$R^3$ represents $C=OR^4$, $C=SR^4$ or $(CH_2)_2COOR^5$ wherein
$R^4$ represents a hydrogen atom or one of the groups $OR^5$ or $NHR^5$ wherein
$R^5$ designates aryl or $C_1$–$C_8$ alkyl, each optionally substituted by halogen,
n represents a number of methylene from 3 to 13 and each X independently represents H or a halogen.

Formula (I) and formula (II) have in common the part $C—(CH^2)_n—CH_2—R^1$

In the specification and claims the term:
halogen is a generic term designating Cl, Br, I and/or F;
alkyl has the meaning of straight chain or branched alkyl;
aryl has the meaning of aromatic, mono- or polycyclic hydrocarbon rings such as for example and preferred; napthyl, anthranyl, phenanthryl, especially phenyl and benzyl.

Preferred is the use of compounds of formula (I) or (II) wherein
represents $NR^2R^3$ wherein
represents a hydrogen atom or $C_1$–$C_4$ alkyl and
represents $C=OR^4$ wherein
$R^4$ represents a hydrogen atom or one of the groups $OR^5$ wherein
represents aryl or $C_1$–$C_8$ alkyl, each optionally substituted by halogen.

Especially preferred is the use of compounds of formula (I) or (II) wherein
$R^1$ represents $NR^2R^3$ wherein
$R^2$ represents a hydrogen atom and
$R^3$ represents $C=OR^4$ wherein
$R^4$ represents a hydrogen atom.

Especially preferred is also the use of compounds of formula (I) or (II) wherein
$R^1$ represents $NR^2R^3$ wherein
$R^2$ represents a hydrogen atom and
$R^3$ represents $C=OR^4$ wherein
$R^4$ represents $OR^5$ wherein
$R^5$ represents methyl, ethyl, n- or i-propyl, n-, s-, i- or t-butyl, or phenyl that is optionally substituted by halogen or benzyl that is optionally substituted by halogen.

Preferred is the use of compounds wherein n represents a number of methylene groups from 6 to 11, most preferably from 6 to 10.

Preferred is the use of compounds of formula (I) wherein each X is a hydrogen.

Alternatively, in the above formulae (I) and (II),
$R^1$ represents $N=CR^6R^7$ wherein
$R^6$ represents a hydrogen atom, C1–C6-alkyl or aryl and
$R^7$ represents C1–C6-alkyl or aryl, each optionally substituted by halogen, preferably
$R^1$ represents $N=CR^6R^7$ wherein
$R^6$ represents a hydrogen atom, methyl or optionally halogen-substituted aryl, and
$R^7$ represents $C_1$–$C_4$ alkyl or optionally halogen substituted aryl, and especially preferably $R^1$ represents $N=CR^6 R^7$ wherein
represents methyl, ethyl, n- or i-propyl, n-, s-, i- or t-butyl, or preferably a hydrogen atom and
$R^7$ represents methyl, ethyl, n- or i-propyl, n-, s-, i- or t-butyl, or phenyl.

The present invention also provides a method to prevent settlement on surfaces by marine or freshwater fouling organisms which comprises contacting said organisms or the locus thereof with at least one compound of formula III or IV.

$$CH_3-(CH_2)_n-CH(CH_2CH_3)R^1 \quad (III)$$

$$(Bu-CH_2-C(CH_3)_2 R^1 \quad (IV)$$

wherein $R^1$, $R^2$, $R^3$, $R^4$, $R^5$, $R^6$, $R^7$, n and X have the meaning and preferred meanings described above in connection with formulae (I) and (II).

The above-menbtoned compounds (hereinafter also referred to as "alkylamine derivatives") are accessible by standard procedures of organic chemistry, which can be adapted to the corresponding amines. The starting alkyl- or alkenylamines are commercially available. The halogenated amines can be easily prepared starting from the alkenylamines or the corresponding ζ-hydroxyalkylamine. In the following general schemes the synthesis of the different derivatives is outlined. For reasons of simplification the synthesis routes are outlined for structure (I) with n=8 and each X=H. The reaction sequences can be adapted easily to all the other amines with other structures and also to mixtures of them.

Synthesis of Compounds with Structure a

Compounds of formula a are accessible via acylation of undecylamine with ethylformate (see Organic syntheses Vol. V, 1973, 300) or with acetic anhydride (see Vogel, "Practical organic chemistry", 1957, 652) or with an acid chloride using Schotten-Baumann conditions (see Houben-Weyl Vol. 11/2 1958, 478).

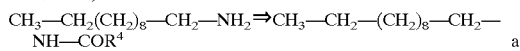     a

Synthesis of Compounds with Structure b

Compounds of formula b are accessible via acylation of undecylamine with a chloroformic ester in an inert solvent with a base as HCl acceptor (see Houben-Weyl Vol.8, 1952, 137; ibid. Vol. 11/2, 1958, 27).

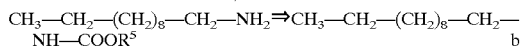     b

Synthesis of Compounds with Structure c

Schiff-bases of undecylamine (IV) are accessible via condensation of undecylamine with an aldehyde or a ketone (Houben-Weyl, Vol. 11/2, 1958, 74).

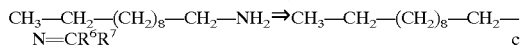     c

Synthesis of Compounds with Structure d

Ureas of formula d can be synthesized by reacting undecylamine with an isocyanate in an inert solvent (see Houben-Weyl, Vol E4, 1983, 352).

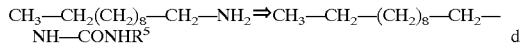     d

Undecylisonitrile can be synthesized from N-formyl undecylamine through reaction with phosphoryl chloride in the presence of diisopropylamine in dichloromethane (Synthesis, 1985, 400).

Undecylisocyanate can be synthesized from undecylamine through reaction with N,N'-carbonyldiimidazole (see Katritzky et al. "Comprehensive organic functional group transformations", Vol 5, 1995).

All other derivatives can be synthesized in analogous manner as described for undecylamine.

DETAILED DESCRIPTION OF THE PREFERRED EMBODIMENT

A fouling organism that may be combated or controlled by the method of the invention can be any marine or freshwater organism that can attach to an inner or outer surface of a structure that is submerged or in continuous contact with water. Accordingly, the invention provides for the use of the alkylamine derivatives for controlling and/or combating aquatic (marine and/or freshwater) fouling organisms. Exemplary organisms include algae, including members of the phyla Chlorophyta, Phaeophyta and Rhodophyta; tunicates, including members of the class Ascidiacea such as *Ciona intestinalis, Diplosoma listerianum* and *Botiyllus sclosseri,* and members of the class Hydrozoa including *Clava squamata, Hydractinia echinata, Obelia geniculata* and *Tubualia larynx;* bivalves including *Mytilus edulis, Cassostrea virginica, Ostrea edulis, Ostrea chilensia, Lasaea rubra* and members of the family Dreissenidae (or zebra mussels) and members of the family Corbuculidae (or Asiatic clams), bryozoans including *Electra pilosa, Conopeum reticulatum, Bugula neritina* and *Bowerbankia gracilis,* polychaete worms including *Hydroides norvegica, Pomatoceros triqueter, Mercierella enigmata* and *Spirorbis* spp. spp.; sponges and members of the class Cirripedia (barnacles) such as *Balanus amphitrite, Lepas anatifera, Balanus balanus, Balanus balanoides, Balanus hameri, Balanus creatus, Balanus improvisus, Balanus galeatus, Balanus eburneus, Elminius modestus, Balanus tulipiformis* and *Balanus perforatus.*

Organisms of the genus *Balanus* are frequent foulers of aquatic structures. Specific fouling organisms to which this invention is especially directed include barnacles, zebra mussels, algae, diatoms, hydroids, bryozoa, ascidians, worms and Asiatic clams, but also the bacterial slime.

Among the aquatic structures which may be protected by the method of invention are any submerged or partially submerged structure, either mobile or stationary, such as a fishnet, boat, ship, piling, cooling tower, pipeline, standpipe, exchanger, dam, intake screen or the like.

In actual practice, antifouling compounds may be brought into contact with a fouling organism by:

coating the aquatic structure with an antifouling paint containing the required effective amount of one or more antifouling compounds in such a way that the said compounds are released at a sufficiently high level so that the protected surface area stays fouling free during the desired service life of the antifouling coating;

more generally, incorporating. for a good antifouling action, the required effective amount of one or more antifouling compounds in the surface layer of the aquatic structure in such a way that the structure is protected against foulers by a constant release of the said compounds;

alternatively, releasing an antifouling-effective amount of said compounds directly into the aquatic environment surrounding the structure to be protected;

or any other method in general wherein the said compounds come in contact with the fouling organisms.

The amount of antifouling compounds and particularly of alkylamine derivative to be used in the method of the invention will vary according to the specific compound used, the identity of the fouling organism to be controlled, the degree of fouling pressure of the surrounding aquatic environment, the water temperature, the mode of contact and the like.

The alkylamine derivatives can be used as individual active compounds or else in combination with active compounds usually employed in the antifouling sector.

These can be used in combination with heavy metals, such as Cu, or heavy metal compounds, such as, for example, bis(trialkyltin) sulphides, tri-n-butyl laurate, copper(I) oxide, triethyltin chloride, tri-n-butyl(2-phenyl4-chlorophenoxy)-tin, tributyltin oxide, molybdenum disulfide, antimony oxide, polymeric butyltitanate, phenyl-(bispyridine)-bismuth chloride, manganese ethylene-bis-dithiocarbamate, zinc dimethyldithiocarbamate, zinc ethylene-bis-dithiocarbamate, copper(I) ethylene-bis-dithiocarbamate, copper thiocyanate, copper naphthenate, tri-n-butyltin(meth)acrylate copolymers, triphenyltin fluoride and tri-n-butyltin halides such as tri-n-butyltin chloride and tr-n-butyltin fluoride. However, combinations with tin compounds are not preferred because of environmental problems linked to the ban on tin compounds in marine paints.

The action spectrum of the alkylamine derivatives is extended further or particular effects are achieved by these combinations of active compounds. Synergistic effects are obtained in many cases.

Preferred combination partners for the alkylamine derivatives are algicides, such as diuron, dichlorophen, endothal, fentin acetate or quinoclamine, molluscicides, such as fentin acetate, metaldehyde, methiocarb, niclosamide, thiodicarb and trimethacarb, fungicides. such as dichlofluanid, tolylfluanid, iodopropargyl butylcarbamate, fluorfolpet and azoles, such as propiconazole, metconazole, cyproconazole and tebuconazole or conventional antifouling active compounds, such as 2-(N-dimethylthiocarbamoylthioy5-nitrothiazyl, tetrabutyldistannoxane, 2-tert-butylamino4-cyclopropylamino-6-methylthio-1,3,5-triazine, 4,5-dichloro-2-n-octyl-4-isothiazolin-3-one, 2,4.5,6-tetrachloroiso-phthalodinitrile, tetramethylthiuram disulphide, 2,4,6 -trichlorophenylmaleimide, 2,3,5,6-tetrachloro-4-(methylsulphonyl)pyridine, diiodomethylparatryl sulphone, thiabendazol tetra-phenyl-boron-pyridin salt, and the copper and sodium salt of 2-pyridinethiol-1-oxide. The most preferred combination partners are algicides.

The antifouling composition preferably comprises the alkylamine derivatives in concentrations of 0.5 to 60% by weight, more preferably between 1 to 25% by weight.

The invention further relates to compositions comprising polymer/plasticiser blends known to any person skilled in the art of antifouling paints, and an effective amount of one or more antifouling compounds of which at least one is an alkylamine derivative. In a preferred embodiment, said one or more antifouling compounds are alkylamine derivatives. In another preferred embodiment, said antifouling compounds consist of a combination of one or more alkylamine derivatives with one or more algicides.

For application onto structural surfaces, preferred compositions of the invention include a film-forming component such as a polymer resin solution. Exemplary polymer resins include unsaturated polyester resins formed from: a) unsaturated acids or anhydrides, such as maleic anhydride, fumaric acid, itaconic acid and the like; b) saturated acids or anhydrides, such as phthalic anhydride, isophthalic anhydride, terephthalic anhydride, tetrahydrophthalic anhydride, tetrahalophthalic anhydride, adipic acid, sebacic acid, and the like; c) glycols, such as ethylene glycol and the like; d) vinyl monomers, such as styrene, vinyl toluene, chlorostyrene, bromostyrene, acrylates like methylmethacrylate, ethylene glycol dimethacrylate and the like. Other suitable resins include vinyl ethers (like vinyl-isobutyl ether), copper and zinc acrylates, triorganosilyl acrylates, titanium acrylates, vinyl ester-, vinyl acetate-, and vinyl chloride-based resins, elastomeric components, vulcanized rubbers, rosins, metalresinates and urethane-based resins.

For further description of components common in antifouling paints see Ungerer in Chem.Ind. 1985, 37, 730 and Williams in Antifouling Marine Coatings, Noyes, Park Ridge, 1973.

EXAMPLE 1

N-formyl Noram C (1)

The starting material Noram C (amine of Coprah) is a mixture of dodecylamine and tetradecylamine. It is described as amine of Coprah of technical grade and was used in the following synthesis without further purification.

A solution of Noram C (1.5 g) dissolved in 3.5 ml of ethytformate was kept at 60° C. during 3 h. Evaporation of the solvent furnished 1.8 g (yield 98%) of N-formyl Noram C (1:1 mixture of N-formyldodecylamine and N-formyltetradecylamine).

Characterisation $^1$H NMR (CDCl$_3$, TMS, δ, J in Hz); 8.16 (1H, s), 5.70 (1H, m), 3.24 (2H, m), 1.20 to 2.00 (±21H, m), 0.88 (3H, t, J=7); EIMS: peaks at m/z 241 (M$^+$ of C-14), 213 (M$^+$ of C-12), 198, 184, 170, 156, 142, 128, 114, 100, 58; IR (film): 3277, 3050, 2928, 2857, 1667, 1543, 1465, 1388 cm$_{-1}$ An evaluation of the marine antifouling activity of this compound is reported below, in vitro and in marine paints.

EXAMPLE 2

N-methoxycarbonyl-6-bromohexylamine (2)

To a stirred solution of 6-aminohexanol in 50 ml of water basified with 11 g of K$_2$CO$_3$, was added 4.03 g of methylchloroformate at room temperature. After one night the resulting aqueous solution was extracted with 3×50 ml of dichloromethane. The organic phases were combined, evaporated to dryness and the residue was filtered over silica gel. This furnished 1.36 g (yield 91%) of N-methoxycarbonyl-6-aminohexanol as a white solid. Then, to a solution of N-methoxycarbonyl-6-aminohexanol (200 mg) in dichloromethane (5 ml) was added 361 mg of triphenylphosphine and 832 mg of tetrabromomethane.

The resulting solution was stirred at room temperature for 20 h. After evaporation of the solvent the solid residue was chromatographed on a column of silica gel (eluent: hexane/acetone:1). This yielded pure N-methoxycarbonyl-6-bromohexylamine (209 mg; yield 77%).

Characterisation: $^1$H NMR (CDCl$_3$, TMS, δ, J in Hz): 4.66 (1H), 3.66 (3H, s), 3.40 (2H, t, J=7), 3.17 (2H, m), 1.86 (2H, m), 1.20 to 1.60 (6H, m); EIMS: peaks at m/z 237 and 239 (M$^+$), 222, 206, 162, 158, 88 An evaluation of the marine antifouling activity of this compound is reported below, in vitro and in marine paints.

EXAMPLE 3

N-formyl-10,11-dibromoundecylamine (3)

Commercially available 11-aminoundec-1-ene (1 g) is dissolved in ethyl formate (1.5 ml). The reaction mixture is kept at 50° C. for 3 h. Then, evaporation of the liquid phase under vacuum furnished almost quantitatively N-formyl-11-aminoundec-1-ene (1.18 g). To a stirred solution of the latter (0.5 g) in chloroform (1 ml) and pyridine (0.2 ml) is added dropwise a solution of dibromide in chloroform (2M, 1.4 ml). During addition the temperature of the mixture is maintained at 0° C. The solution is kept at 0° C. during 30 min. then diluted with dichloromethane (10 ml) and washed with saturated solutions of sodium bicarbonate (10 ml), 10% HCl (2×10 ml) and 10% sodium bisulfite (2×10 ml) successively. The organic layer is evaporated to dryness under vacuum and the solid residue is chromatographed over a silica gel column (eluent: hexane/acetone 1:1). This furnished 639 mg of pure N-formyl-10,11-dibromoundecylamine (yield 70%).

Characterisation: $^1$H NMR (CDCl$_3$, TMS, δ, J in Hz): 8.17 (1H, s), 5.50 (1H, m), 4.17 (1H, m), 3.85 (1H, dd, J=4 and 10), 3.63 (1H, t, J=10), 3.25 (2H, m), 1.30 to 2.12 (16H, m); EIMS: peaks at m/z 355, 357 and 359 (M$^+$), 276, 196; IR (film): 3294, 3065, 2924, 1671, 1540 cm$^{-1}$.

An evaluation of the marine antifouling activity of this compound is reported below, in vitro and in marine paints.

EXAMPLE 4

N-formyl-N-methyl Noram C (4)

N-formyl Noram C (1; 506 mg) dissolved in anhydrous THF (5 ml) was added slowly to a suspension of LiAlH$_4$ (830 mg) in anhydrous THF. The resulting reaction mixture was refluxed for 3 h and then cooled to room temperature. excess of LiAlH$_4$ was then carefully destroyed by adding water (4 ml). The aqueous phase was extracted with CH$_2$Cl$_2$ (3×10 ml). The organic phases were combined, filtered and evaporated to dryness under reduced pressure. This furnished a crude sample of N-methyl Noram C (440 mg ; yield: 93%), 399 mg of which was dissolved in ethylformate (10 ml). The solution was refluxed for 70 h and then evaporated to dryness under vacuum. The resulting solid residue was chromatographed over a silica gel column (eluent: hexane/acetone 9:1) furnished 404 mg of pure N-formyl-N-methyl Noram C.

Characterisation: $^1$H NMR (CDCl$_3$, TMS, δ, J in Hz); 8.03 (1H, s), 3.21 (0.6H, t, J=7), 3.31 (1.4H, t, J=7), 2.92 (0.6H, s), 2.85 (1.4H, s), 1.91 (0.6H, m), 1.54 (1.4H, m), 1.26 (±20H, m), 0.88 (3H, t, J=7); EIMS: peaks at m/z 256 (M$^+$+H of C-14), 228 (M$^+$+H of C-12), 226, 212, 210, 200, 198, 184, 170, 156, 142, 128, 114, 100, 86, 73 (100); IR, (film) 2937, 2853, 1681, 1488 cm$^{-1}$.

An evaluation of the marine antifouling activity of this compound is reported below, in vitro and in marine paints.

EXAMPLE 5

N-acetyl Noram C (5)

Acetic anhydride (1 ml) was added slowly at room temperature to a solution of Noram C in pyridine (1 ml). The reaction mixture was stiffed at room temperature for 30 min. After addition, of ethanol (2 ml) the solution was kept at room temperature for again 30 min, and then evaporated to dryness under reduced pressure. The resulting solid was dissolved in CH$_2$Cl$_2$ (10 ml) and the organic phase washed successively with diluted HCl and with diluted NH$_4$OH. Then, the organic phase was evaporated to dryness under reduced pressure and the resulting residue was chromatographed over a column of silica gel (eluent: hexane/acetone 5:5). This furnished 1.356 g of pure N-acetyl Noram C as a white solid (yield 94%).

Characterisation: $^1$H NMR (CDCl$_3$, TMS, δ, J in Hz): 5.7 (1H, bs), 3.1 (2H, m), 1.94 (3H, s), 1.47 (2H, m), 1.24 (±20H, m), 0.83 (3H, t, J=7); EIMS: peaks at m/z 255 (M$^+$ of C-14) and 227 (M$^+$ of C-12), 212, 199, 184, 170, 156, 142, 128, 114, 100, 86, 73 (100); IR (film): 3284, 3094, 2919, 2850, 1642, 1567 cm$^{-1}$ An evaluation of the marine antifouling activity of this compound is reported below, in vitro and in marine paints.

EXAMPLE 6

3-Noram C Propionic Acid Methyl Ester (6)

A solution of ethyl acrylate (473 mg) in methanol (5 ml) was added dropwise at room temperature, to a solution of Noram C in methanol (10 ml). The reaction mixture was stirred for 17 h. Evaporation of the solvent under reduced pressure, followed by a chromatography of the solid residue over a column of silica gel (eluent hexane/acetone 5:5) furnished compound 6 (888 mg) in a 65% yield.

Characterisation: $^1$H NMR (CDCl$_3$, TMS, δ, J in Hz): 3.68 (3H, s), 2.88 (2H, t, J=7), 2.60 (2H, t, J=7), 2.52 (2H, t, J=7), 1.46 (2H, m), 1.26 (±20H, m), 0.88 (3H, t, J=7); EIMS: peaks at m/z 299 (M$^+$ of C-14) and 271 (M$^+$ of C-12), 256, 242, 228, 226, 214, 212, 198, 116 (100), 84; IR (film) 2957, 2858, 1746, 1471 cm$^{-1}$.

An evaluation of the marine antifouling activity of this compound is reported below, in vitro and in marine paints.

EXAMPLE 7

N-formyl-11-bromo-undecyl-1-amine (7)

Di-tert-butyldicarbonate (2.8 g) was added at room temperature to a solution of commercially available 1-aminoundec-10-ene (2 g) in dry THF (40 mL). The solution was stirred at room temperature for 15 h. Then the solvent was evaporated and the solid residue submitted to bulb-to-bulb distillation to furnish N-tert-butoxycarbonyl-1-aminoundec-10-ene (2.96 g, yield: 93%). To the latter (500 mg) was added 278 mL of borane-dimethylsulfide complex (10 M) in THF at 15° C. under an atmosphere of dry nitrogen. The reaction mixture was allowed to reach +10° C. After 2 h. the excess of borane complex was destroyed by addition of a few drops of water, 1 mL of NaOH (20%) and 1 mL of H$_2$O$_2$ (33%). After one hour at room temperature, the resulting reaction mixture was poured onto 30 mL of water and extracted with 2×30 mL of CH$_2$Cl$_2$. The organic phases were combined and evaporated to dryness. The solid residue was flash chromatographed on a Silica gel column. This furnished N-tert-butoxycarbonyl-1-aminoundecan-11-ol (325 mg, yield: 66%). Triphenylphosphine (273 mg) and carbon tetrabromide (667 mg) were successively added to a stirred solution of N-tert-butoxycarbonyl-1-aminoundecan-11-ol (300 mg) in CH$_2$Cl$_2$ (5 mL). After 3 h at room temperature, the solvent was evaporated and the residue chromatographed on a Silica gel column (eluent: CH$_2$Cl$_2$) leading to N-tert-butoxycarbonyl-11-bromoundecyl-1-amine (300 mg, yield: 82%). Then, trifluoroacetic acid (1 mL)

added to a solution of this amine (222 mg) in CH$_2$Cl$_2$ (5 mL). After 1 h at room temperature, the reaction mixture was poured onto an aqueous solution of KOH (1 M, 10 mL). The organic layer was evaporated to dryness and the residue dissolved in ethyl formate (10 mL). After one night at room temperature, the solvent was evaporated and the solid residue flash chromatographed on a Silica column (eluent: acetone-hexane) leading to 125 mg of N-formyl-11-bromoundecyl-1-amine (yield: 71%).

Characterisation: EIMS: peaks at m/z 279 and 277 (2, M$^+$), 198 (88), 170 (23), 114 (28), 100 (53), 72 (45), 59 (100); $^1$H NMR (CDCl$_3$, TMS, δ, J in Hz): 8.1 (1H, s), 5.44 (1H, bs), 3.41 (2H, t, J=7), 3.30 (2H, q, J=7), 1.85 (2H, quint, J=7), 1.50 (4H, m), 1.29 (12H, m).

An evaluation of the marine antifouling activity of this compound is reported below, in vitro and in marine paints.

EXAMPLE 8

N-formyl-1-aminoundec-10-ene (8)

A solution of commercially available 1-aminoundec-10-ene (1 g) dissolved in ethyl formate (3.5 mL) was kept at 50° during 3 h. Evaporation of the solvent yielded 1.18 g of N-formyl-1-aminoundec-10-ene (yield: 99%).

Characterisation: EIMS: peaks at m/z 197 (M$^+$), 168, 156, 154, 152, 140, 126, 114, 100, 58; $^1$H NMR (CDCl$_3$, TMS, δ, J in Hz): 8.15 (1H, s), 5.81 1H, m), 5.65 (1H, bs), 4.98 (1H, dd, J=17/1), 4.93 (1H, dd, J=10/1), 3.30 (2H, q, J=7), 2.03 (2H, q, J=7), 1.50 (2H, m), 1.29 (12H, m); IR (film): 3285, 3072, 2926, 2850, 1660 cm$^{-1}$ An evaluation of the marine antifouling activity of this compound is reported below, in vitro and in marine paints.

EXAMPLE 9

N-formyl-1-aminoundecane (9)

N-formyl-1-aminoundec-10-ene (467 mg) was dissolved in ethanol (2 ml). Pd/C (46 mg) was added and the mixture submitted to hydrogenation at atmospheric pressure during 10 h. The reaction mixture was filtered through a short column of celite and the solvent evaporated under vacuo. This yielded N-formyl-1-aminoundecane (468 mg, yield: 100%) as a white solid Characterisation: EIMS: peaks at m/z 199 (M$^+$), 70, 156, 142, 128, 114, 100, 72, 59; $^1$H NMR (CDCl$_3$, TMS, δ, J in Hz): 8.7 (1H, s), 5.55 (1H, bs), 3.26 (2H, q, J=7), 1.50 (2H, m), 1.27 (12H, m), 0.88 (3H, t, J=7); IR (film): 3277, 3071, 2919, 2850, 1645 cm$^{-1}$ An evaluation of the marine antifouling activity of this compound is reported below, in vitro and in marine paints.

EXAMPLES 10 to 34

Examples marked (*) are outside the invention claimed in the present application

| Example | Structure | EI-MS [m/z] | IR [cm$^{-1}$] |
|---|---|---|---|
| 10 | 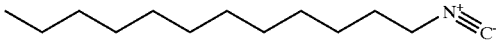 | (M − H)$^+$ at 194 | 2143 |
| 11 | 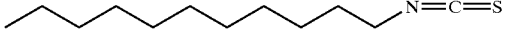 | M$^+$ at 227 | 2098<br>2180 |
| 12 | 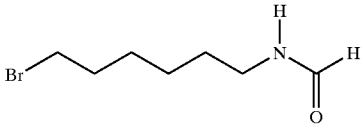 | (M + H)$^+$ at 208/210 | 1653<br>3280 |
| 13 | 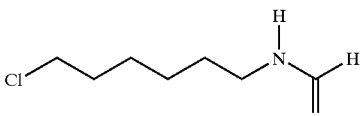 | (M + H)$^+$ at 164/166 | |
| 14 | 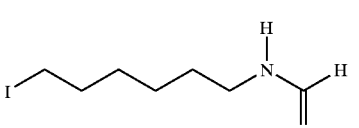 | M$^+$ at 217 | |
| 15 (*) | 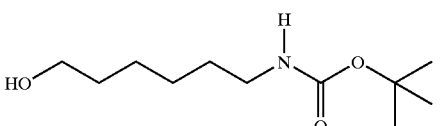 | (M + H)$^+$ at 256 | |
| 16 (*) | 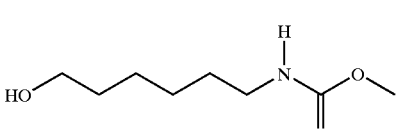 | (M + H)$^+$ at 176 | |
| 17 (*) | 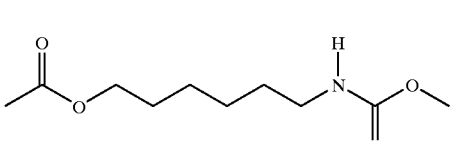 | M$^+$ at 217 | |

| Example | Structure | EI-MS [m/z] | IR [cm$^{-1}$] |
|---|---|---|---|
| 18 = 2 | Br-(CH₂)₅-NH-C(=O)-O-CH₃ | M⁺ at 237/239 | |
| 19 | Br-(CH₂)₅-NH-C(=O)-O-C(CH₃)₃ | M⁺ at 279/281 | |
| 20 (*) | CH₃-C(=O)-O-(CH₂)₅-NH-CHO | (M + H)⁺ 188 | |
| 21 (*) | CF₃-C(=O)-O-(CH₂)₅-NH-CHO | M⁺ 241 | |
| 22 | Br-(CH₂)₁₁-NH-C(=O)-O-C(CH₃)₃ | M⁺ at 349/351 | |
| 23 | Br-(CH₂)₁₁-N=C=S | (M − H)⁺ at 274/276 | 2268 |
| 24 | Br-(CH₂)₁₁-N⁺≡C⁻ | | 2142 |
| 25 | (CH₃)CHBr-(CH₂)₈-NH-CHO | | 1651 |
| 26 (*) | CH₃-(CH₂)n-CH₂-NH-SO₂-C₆H₄-CH₃ <br> n = 9 and 11 | M⁺ at 339 and 367 | 3282 <br> 1325 <br> 1157 |
| 27 (*) | CH₃-(CH₂)n-CH₂-NH-SO₂-CH₃ <br> n = 9 and 11 | (M + H)⁺ at 264 and 292 | 3272 <br> 1320 <br> 1153 |
| 28 (*) | CH₃-(CH₂)n-CH₂-NH-CH₂-CH₂-C(=O)-OH <br> n = 9 and 11 | M⁺ at 257 and 285 | 2800 <br> 1725 |

-continued

| Example | Structure | EI-MS [m/z] | IR [cm$^{-1}$] |
|---|---|---|---|
| 29 (*) | 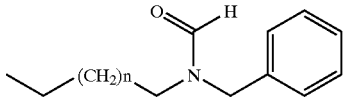 n = 9 and 11 | M$^+$ at 303 and 331 | 1672 |
| 30 (*) | 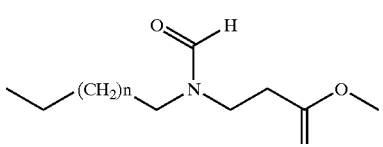 n = 9 and 11 | (M − H)$^+$ at 298 and 326 | |
| 31 (*) | 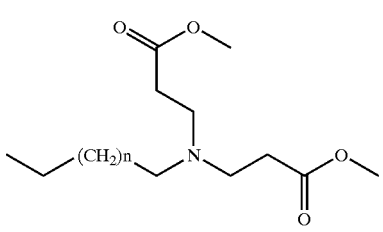 n = 9 and 11 | M$^+$ 357 and 385 | 1747 |
| 32 (*) | 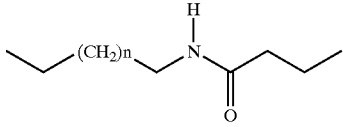 n = 9 and 11 | M$^+$ 255 and 283 | 3293<br>1638 |
| 33 | 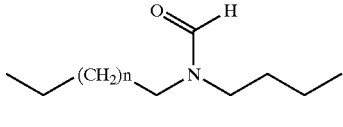 n = 9 and 11 | | 1680 |
| 34 | 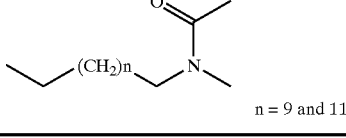 n = 9 and 11 | M$^+$ at 241 and 269 | 1652 |

Evaluation of Marine Antifouling Activity of Test Compounds

The rate of settlement of laboratory reared cyprid larvae of the barnacle Balanus amphitrite was determined for testing the activity of candidate antifouling compounds.

Settlement Assay

Tests are carried out in four replicates in sterile polystyrene multi well plates. Between 25 and 40 cyprid larvae are injected in the dishes containing either 2 ml of test solution (see below), solvent control or a positive control (dichloro-n-octyl-isothiazolinone).

Dishes are incubated for 24 h at a temperature of 27° C. ±2. After incubation the cyprids are screened for signs of toxicity. The test is terminated by addition of a drop of 20% formaldehyde and the numbers of settled and non-settled larvae are counted.

Settlement is evaluated as follows: 1) non settled: not attached free-swimming cyprids, 2) settled cyprids: attached, but not metamorphosed cyprids, 3) barnacles: attached juvenile barnacles.

Categories 2 and 3 are considered to be settled. Percentage settlement in test solution is compared with controls. Estimates of the median effect concentration (EC50) after 50 h are calculated using the Spearman-Karber method.

All seawater used is of natural origin and filtered unto 0.2 μm. Stock solutions of test compounds are prepared by dissolving an amount of test substance in a suitable solvent and subsequent addition of seawater.

The stock solutions are used to prepare several dilution serial in seawater. Controls are made of seawater, or, if appropriate, in a mixture of seawater and solvent.

The solvent concentration in the controls is equal to the highest concentration in the test solution. As an internal standard (positive control) a concentration range 0 to 5 ppm dichloro-n-octylisothiazolinone is included in each test.

Test Results

| Compound | EC50 for settlement inhibition in ppm |
|---|---|
| 1 | |
| 2 | |
| 3 | |
| 4 | 1.80 | been tested by application of the paints on raft panels. At first the steel panels had been protected with a standard anticorrosive system for marine environments (300 μm in dft). The to be tested antifouling paint had been applied in 2 layers with a total dry film thickness between 200 and 300 μm. Finally the panels were subjected to a static immersion test on rafts at sea harbors in Holland. The paints were inspected for the presence of fouling (% of area covered with fouling organisms) and of film defects every two months. The tested paint formulations are represented in Table 1.

TABLE 1

Tin-free ablative antifouling formulations (model coatings, MC) for the evaluation of new biocides (all in w %). Composition of the formulation code: Structure code + Model coating code.

| Ingredient | MC-1 A/B/C | MC-6/7 | MC-10 A/B | MC-2/3 | MC-4 | MC-5 | MC-8/9 | MC-11 |
|---|---|---|---|---|---|---|---|---|
| Neocryl B725 | 5 | 5 | 5 | 5 | 5 | 5 | 5 | 5 |
| Rosin | 10 | 10 | 10 | 10 | 10 | 10 | 10 | 10 |
| Platicizer*** | 2 | 2 | 2 | 2 | 2 | 2 | 2 | 2 |
| Cu2O | 35 | 0 | 0 | 35 | 35 | 50 | 0 | 0 |
| Universal biocide | 0 | 0 | 4/8 | 0 | 0 | 0 | 0 | 0 |
| New barnaclecide | 0 | 1/2/4 A/B/C | 0 | 0 | 0 | 0 | 0 | 0 |
| Seanine**/Irgarol | 0 | 3/3 | 0 | 3/3 | 0 | 0 | 3/3 | 0 |
| New Algicide | 1/2/3 | 0 | 0 | 0 | 0 | 0 | 0 | 0 |
| Iron oxide | 5 | 5 | 5 | 5 | 5 | 3 | 5 | 5 |
| Talc | 5 | 20 | 20/15 | 5 | 8 | 3 | 20 | 20 |
| Zinc oxide | 5 | 15 | 15 | 5 | 5 | 3 | 20 | 20 |
| Antisagging/thix agent | 1.5 | 1 | 1 | 1.5 | 1.5 | 1.5 | 1 | 1 |
| xylene* to 100% | 30.5–27.5 | 38–35 | 38–39 | 28.5 | 28.5 | 22.5 | 34 | 37 |

*Only indicative. Used amount will strongly depend on the biocide used. Paint viscosity should be in the range of 12–16 dPas. Always including 0.5% of ethanol for activation of bentone agent.
**Seanine (trade mark) is delivered as a 30% solution in xylene. The value in the table is for 100% active ingredient. The xylene of the Seanine solution was considered as added solvent.
***Plasticizer stands for plasticizer, e.g.. Santicizer 261 (phthalate-type).

-continued

Test Results

| Compound | EC50 for settlement inhibition in ppm |
|---|---|
| 5 | 1.70 |
| 6 | |
| 7 | |
| 8 | 0.60 |
| 9 | |
| 25 | |
| reference* | |

*= 4,5-dichloro-n-octylisothiazolinone

Evaluation of Test Compounds in Paints

Compounds with formula (I) and (II) have proven their efficacy in a number of paint formulations. The compounds do not require a special treatment and can be used in all technologies that are commonly used in the antifouling field. The rosin-based ablative antifouling-technology will be used here as an example to demonstrate the use and performance of the claimed compounds, but should not be considered as a limitation to its use. The claimed compounds have proven their performance in other antifouling technologies (antifouling binder system) as well.

The prepared paints have been evaluated on can stability, adhesion and film defects. The antifouling performance has Specification and Source of Ingredients:
INERT BINDER: NEOCRYL B725, ZENECA.
ROSIN: INDONESIAN GUMROSIN WW (De Monchi, NL)
SANTICIZER 261: MONSANTO
CUPROUS OXIDE: PAINT GRADE, RED, NORDDEUTSCHE antifouling FINERIE/NORDOX
SEANINE: ROHM AND HAAS
IRGAROL 1051: CIBA GEIGY
IRON OXIDE: BAYFERROX 130 BM, BAYER
TALC: FINNTALC M15, SUOMEN TAKKI OY; MICROTALC A.T.1, NORWEGIAN TALC
ZINC OXIDE: EP/M, DIRECT OR AMERICAN PROCESS, UNION MINIERE/ZINKWIT NL, PURITY >99%.
ANTI-SAGGING: BENTONE 38, RHEOX
XYLENE: NORMAL GRADE
ETHANOL: DENATURATED WITH 5% METHANOL, 4% WATER.
Alternative Options ( No Substitutes) for Raw Materials:
INERT RESIN/ROSIN RATIO: 11/4 OR 7.5/7.5.
ALTERNATIVE PLASTICIZER/INERT BINDER: TCP/LAROFLEX.
TCP: TRICRESYLPHOSPHATE, DISFLAMOLL TKP, BAYER
LAROFLEX MP 35: BASF
BENTONITE: SD2, RHEOX Further explanations to Table 1:
1. Model coatings of type 1 (MC-1A/B/C) are for the evaluation of the algicidal properties of the claimed structures at three different representative weight-% next to 35% cuprous oxide. Good performing references are model coating MC-2 and MC-3 [35% cuprous oxide+3% Seanine (MC-2) or 35% cuprous oxide+3% Irgarol (MC-3)]. Base level references are "cuprous oxide only" formulations [cuprous oxide only (35% (MC4) and 50% level (MC-5)].
2. Model coatings of type 6 and 7 are for the evaluation of the activity of the claimed structures against "hard fouling" in combination with two different types of algicides: claimed structure (1/2/4%; MC-6-A/B/C)+3% Seanine or claimed structure (1/2/4%; MC-7-A/B/C)+3% Irgarol). Base level references are "algicide only" formulations with 3% Seanine (MC-8) or 3% Irgarol (MC-9).
3. Model coatings of type 10 (MC-10A/B) evaluate the total spectrum of biocidal activity by using the claimed structure as only biocide at 2 levels (4 and 8 w %). Good performing references are "cuprous oxide only" formulations [cuprous oxide 35% (MC-4) and 50% (MC-5)]. As blank serves model coating 11 (MC-1 1) containing no biocide at all.

The claimed structures were tested at several levels of dosage with and without an algicide as co-biocide. The following formulations were used for comparison: formulations with cuprous oxide, formulations with cuprous oxide and commercial co-biocides, a blank and two formulations that only contained the co-biocide and finally a commercial tributyltin-releasing self polishing system.

The paints were evaluated for can stability by storing 250 ml of paint at 40° C. for 3 months and measuring the fineness and the viscosity. Large changes during storage were not observed for any of the described formulations.

Adhesion and film defects were checked on raft panels at regular intervals during the fouling season. The adhesion was in all cases acceptable to good and no film defects were observed.

The antifouling performance after 1-year immersion on a raft test site in a seawater harbor in Holland is presented in table 2. They demonstrate that the claimed structures offer a protection against fouling just as well as cuprous oxide. An even better protection can be obtained by combining claimed structures with co-biocides like the algicides that are commonly used for antifoulings.

TABLE 2

Antifouling performance with respect to slime, algae and hard fouling after one year immersion (Dutch harbor, sea water). Classifications: good (G) satisfactory (S), failure (F)

| PERFORMANCE | SLIME | ALGAE | HARD FOULING |
|---|---|---|---|
| Good (G) | Not present | Not present | Not present |
| Satisfactory (S) | Some light slime | <20% of area covered mainly edge effects. | <3% of total area covered mainly edge effects. |
| Unsatisfactory (F) | Overall covered | >20% of area covered | >3% of area covered |

| Paint example | 1st Active Ingredient | 2nd Active Ingredient | Model coating | Slime | Algae | Hard fouling | Overall |
|---|---|---|---|---|---|---|---|
| 1, 12, 23, 34, 45, 56, 67, 78, 89, 100 | 35% Cu$_2$O | 1% of 1, 2, 3, 4, 5, 6, 7, 8, 9 | 1A | S | S | G | S |
| 2, 13, 24, 35, 46, 57, 68, 79, 90, 101 | 35% Cu$_2$O | 2% of 1, 2, 3, 4, 5, 6, 7, 8, 9 | 1B | S | G | G | S |
| 3, 14, 25, 36, 47, 58, 69, 80, 91, 102 | 35% Cu$_2$O | 3% of 1, 2, 3, 4, 5, 6, 7, 8, 9 | 1C | G | G | G | G |
| 4, 15, 26, 37, 48, 59, 70, 81, 92, 103 | 1% of 1, 2, 3, 4, 5, 6, 7, 8, 9 | 3% Seanine | 6A | S | G | F | F |
| 5, 16, 27, 38, 49, 60, 71, 82, 93, 104 | 2% of 1, 2, 3, 4, 5, 6, 7, 8, 9 | 3% Seanine | 6B | S | G | S | S |
| 6, 17, 28, 39, 50, 61, 72, 83, 94, 105 | 4% of 1, 2, 3, 4, 5, 6, 7, 8, 9 | 3% Seanine | 6C | G | G | G | G |
| 7, 18, 29, 40, 51, 62, 73, 84, 95, 106 | 1% of 1, 2, 3, 4, 5, 6, 7, 8, 9 | 3% Irgarol | 7A | S | G | F | F |
| 8, 19, 30, 41, 52, 63, 74, 85, 96, 107 | 2% of 1, 2, 3, 4, 5, 6, 7, 8, 9 | 3% Irgarol | 7B | S | G | S | S |
| 9, 20, 31, 42, 53, 64, 75, 86, 97, 108 | 4% of 1, 2, 3, 4, 5, 6, 7, 8, 9 | 3% Irgarol | 7C | S | G | S | S |
| 10, 21, 32, 43, 54, 65, 76, 87, 98, 109 | 4% of 1, 2, 3, 4, 5, 6, 7, 8, 9 | — | 10A | F | S | S | F |
| 11, 22, 33, 44, 55, 66, 77, 88, 99, 110 | 8% of 1, 2, 3, 4, 5, 6, 7, 8, 9 | — | 10B | S | S | G | S |

TABLE 2-continued

Antifouling performance with respect to slime, algae and hard fouling after one year immersion (Dutch harbor, sea water). Classifications: good (G) satisfactory (S), failure (F)

| | | | | | | | |
|---|---|---|---|---|---|---|---|
| Comp. Ex 1 | 35% CU$_2$O | 3% Seanine | MC-2 | G | G | G | G |
| Comp. Ex 2 | 35% CU$_2$O | 3% Irgarol | MC-3 | S | G | G | G |
| Comp. Ex 3 | 35% CU$_2$O | — | MC-4 | S | S | G | S |
| Comp. Ex 4 | 50% CU$_2$O | — | MC-5 | S | G | G | G |
| Comp. Ex 5 | — | 3% Seanine | MC-8 | S | S | F | F |
| Comp. Ex 6 | — | 3% Irgarol | MC-9 | F | S | F | F |
| Comp. Ex 7 | — | — | MC-11 | F | F | F | F |
| Comp. Ex 8 | TBTO | Zineb | — | G | G | G | G |

What is claimed is:

1. Method for preventing settlement of fouling organisms on an aquatic structure, comprising the step of contacting said organisms or the locus thereof with an antifouling effective amount of one or more antifouling compounds of which at least one is an alkylamine derivative of formula (I) or (II):

(I) $XCH_2$—$CHX$—$(CH_2)_n$—$CH_2$—$R^1$ (II) $CH_2$=$CH$—$(CH_2)_n$—$CH_2$—$R^1$ wherein $R^1$ represents an isonitrile or isocyanate moiety, or $NR^2R^3$ wherein $R^2$ represents a hydrogen atom or $C_1$–$C_8$ alkyl and $R^3$ represents C=$OR^4$, C=$SR^4$ or $(CH_2)_2COOR^5$ wherein $R^4$ represents a hydrogen atom or one of the groups $OR^5$ or $NHR^5$ wherein $R^5$ designates aryl or $C_1$–$C_8$ alkyl, each optionally substituted by halogen, n represents a number of methylene from 3 to 13 and each X independently represents H or a halogen.

2. Method according to claim 1, wherein $R^1$ represents $NR^2R^3$ wherein $R^2$ represents a hydrogen atom or $C_1$–$C_4$ alkyl and $R^3$ represents C=$OR^4$ wherein $R^4$ represents a hydrogen atom or one of the groups $OR^5$ wherein $R^5$ represents aryl or $C_1$–$C_8$ alkyl, each optionally substituted by halogen.

3. Method according to claim 2, wherein $R^1$ represents $NR^2R^3$ wherein $R^2$ represents a hydrogen atom and $R^3$ represents C=$OR^4$ wherein $R^4$ represents a hydrogen atom or one of the groups $OR^5$ wherein $R^5$ represents methyl, ethyl, n- or i-propyl, n-, s-, i- or t-butyl, or phenyl that is optionally substituted by halogen or benzyl that is optionally substituted by halogen.

4. Method according to claim 1, wherein n represents a number of methylene from 6 to 11.

5. Method according to claim 4, wherein n represents a number of methylene from 6 to 10.

6. Method according to claim 1, wherein each X represents hydrogen.

7. Method according to claim 1, wherein the alkylamine derivative is used in combination with at least one algicide.

8. Method according to claim 1, wherein the antifouling compounds are incorporated in a surface layer of the aquatic structure.

9. Method according to claim 8, wherein the antifouling compounds are incorporated in an antifouling paint coating the aquatic structure.

10. Paint composition comprising an antifouling effective amount of one or more antifouling compounds of which at least one is an alkylamine derivative of formula (I) or (II):

(I) $XCH_2$—$CHX$—$(CH_2)_n$—$CH_2$—$R^1$ (II) $CH_2$=$CH$—$(CH_2)_n$—$CH_2$—$R^1$ wherein $R^1$ represents an isonitrile or isocyanate moiety, or $NR^2R^3$ wherein $R^2$ represents a hydrogen atom or $C_1$–$C_8$ alkyl and $R^3$ represents C=$OR^4$, C=$SR^4$ or $(CH_2)_2COOR^5$ wherein $R^4$ represents a hydrogen atom or one of the groups $OR^5$ or $NHR^5$ wherein $R^5$ designates aryl or $C_1$–$C_8$ alkyl, each optionally substituted by halogen, n represents a number of methylene from 3 to 13 and each X independently represents H or a halogen.

11. Paint composition according to claim 10, wherein $R^1$ represents $NR^2R^3$ wherein $R^2$ represents a hydrogen atom or $C_1$–$C_4$ alkyl and $R^3$ represents C=$OR^4$ wherein $R^4$ represents a hydrogen atom or one of the groups $OR^5$ wherein $R^5$ represents aryl or $C_1$–$C_8$ alkyl, each optionally substituted by halogen.

12. Paint composition according to claim 11, wherein $R^1$ represents $NR^2R^3$ wherein $R^2$ represents a hydrogen atom and $R^3$ represents C=$OR^4$ wherein $R^4$ represents a hydrogen atom or one of the groups $OR^5$ wherein $R^5$ represents methyl, ethyl, n- or i-propyl, n-, s-, i- or t-butyl, or phenyl that is optionally substituted by halogen or benzyl that is optionally substituted by halogen.

13. Paint composition according to claim 10, wherein n represents a number of methylene from 6 to 11.

14. Paint composition according to claim 13, wherein n represents a number of methylene from 6 to 10.

15. Paint composition according to claim 10, wherein each X represents hydrogen.

16. Paint composition according to claim 10, further comprising at least one algicide.

* * * * *